United States Patent
Pinter et al.

(10) Patent No.: US 10,029,065 B2
(45) Date of Patent: Jul. 24, 2018

(54) SYSTEM AND METHOD FOR INCREASING THE RELAXATION OF A PERSON

(75) Inventors: Robert Pinter, Aachen (DE); Anke Schmeink, Herzongenrath (DE); Cristina Bescos Del Castillo, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 102 days.

(21) Appl. No.: 13/140,041

(22) PCT Filed: Dec. 14, 2009

(86) PCT No.: PCT/IB2009/055728
§ 371 (c)(1),
(2), (4) Date: Jun. 16, 2011

(87) PCT Pub. No.: WO2010/070569
PCT Pub. Date: Jun. 24, 2010

(65) Prior Publication Data
US 2011/0257466 A1    Oct. 20, 2011

(30) Foreign Application Priority Data
Dec. 19, 2008 (EP) .................................. 08172274

(51) Int. Cl.
*A61M 21/02* (2006.01)
*A61M 21/00* (2006.01)
(Continued)

(52) U.S. Cl.
CPC ............. *A61M 21/00* (2013.01); *A61B 5/486* (2013.01); *A61B 5/024* (2013.01);
(Continued)

(58) Field of Classification Search
CPC .. A61M 2021/0005; A61M 2021/0044; A61M 21/00–21/02
(Continued)

(56) References Cited

U.S. PATENT DOCUMENTS 5,348,008 A    9/1994 Bornn et al.
5,634,469 A *  6/1997 Bruder et al. ................ 600/512
(Continued)

FOREIGN PATENT DOCUMENTS

JP    05212117 A    8/1993
JP    08131501 A    5/1996
(Continued)

OTHER PUBLICATIONS

Tiller et al: "Cardiac Coherence: A New, Noninvasive Measure of Autonomic Nervous System Order"; Alternative Therapies in Health and Medicine, Jan. 1996, vol. 2, No. 1, pp. 52-65.

*Primary Examiner* — Thaddeus Cox (57) ABSTRACT

The present invention relates to a system (100) for increasing a degree of relaxation of a person (10) using biofeedback. The system (100) comprises a first physiological parameter determining unit (20) for determining a first physiological parameter of the person (10), a reference parameter providing unit (60) for providing a reference parameter, a correlation determining unit (30) for determining a degree of correlation between the first physiological parameter and the reference parameter and a controller (40) for determining a control information based on the determined degree of correlation for controlling a light source unit (50), wherein in a mode of operation of the system the control information is adapted to control the light source unit (50) by dimming the light source unit and/or changing the
(Continued)

color of the light from the light source unit to warmer color tones having a lower color temperature when the degree of correlation increases.

20 Claims, 8 Drawing Sheets

(51) Int. Cl.
    *A61B 5/0205*     (2006.01)
    *A61B 5/024*     (2006.01)
    *A61B 5/113*     (2006.01)
    *A61B 5/00*     (2006.01)

(52) U.S. Cl.
    CPC ........... *A61B 5/02055* (2013.01); *A61B 5/113* (2013.01); *A61B 5/4806* (2013.01); *A61B 2560/0242* (2013.01); *A61M 21/02* (2013.01); *A61M 2021/005* (2013.01); *A61M 2021/0022* (2013.01); *A61M 2021/0027* (2013.01)

(58) Field of Classification Search
    USPC ..................................................... 600/26, 27
    See application file for complete search history.

(56) References Cited

U.S. PATENT DOCUMENTS

| | | | |
|---|---|---|---|
| 6,554,763 B1 | 4/2003 | Amano | |
| 7,324,609 B1 * | 1/2008 | Hwang et al. | 375/319 |
| 7,966,154 B2 * | 6/2011 | Vock et al. | 702/188 |
| 2005/0143617 A1 * | 6/2005 | Auphan | 600/26 |
| 2005/0187426 A1 * | 8/2005 | Elliott | 600/26 |
| 2005/0215847 A1 * | 9/2005 | Heruth et al. | 600/26 |
| 2007/0083079 A1 * | 4/2007 | Lee et al. | 600/27 |

FOREIGN PATENT DOCUMENTS

| | | | | |
|---|---|---|---|---|
| JP | 2000294388 A | 10/2000 | | |
| JP | 2004259487 A | 9/2004 | | |
| JP | 2005137895 A | 6/2005 | | |
| JP | 2008154681 A | 7/2008 | | |
| JP | 2008301957 A | 12/2008 | | |
| NL | WO 2008017979 A2 * | 2/2008 | | A61B 5/486 |
| WO | 9620639 A1 | 7/1996 | | |
| WO | 0213679 A2 | 2/2002 | | |
| WO | 2006054210 A1 | 5/2006 | | |
| WO | 2008017979 A2 | 2/2008 | | |
| WO | WO 2008090494 A1 * | 7/2008 | | |
| WO | 2009133517 A1 | 11/2009 | | |

\* cited by examiner

SYSTEM AND METHOD FOR INCREASING THE RELAXATION OF A PERSON

FIELD OF THE INVENTION

The present invention relates to a system and a method for increasing a degree of relaxation of a person.

BACKGROUND OF THE INVENTION

In document WO 2006/054210, a system is disclosed for promoting relaxation by controlling the reproduction of audio/video signals based on the determination of a transition between the different sleep phases. In such a system, periodic sounds generated by physiological characteristics, such as heart rate or breathing rate, are acoustically detected by electro-acoustic sensors. Due to the presence of these sensors that can detect any noise or sound in the room where the monitored person is located, the system requires means for differentiating the different acoustic signals to be detected. However, the control of the reproduction of audio/video signals may be not sufficiently accurate because of environmental noise not caused by the heart or by respiration.

SUMMARY OF THE INVENTION

It is an object of the present invention to provide a system for increasing a degree of relaxation of a person, which allows modifying the degree of relaxation with an increased accuracy.

In accordance with the present invention, there is provided a system for increasing a degree of relaxation of a person, the system comprising:
a first physiological parameter determining unit (20) for determining a first physiological parameter of the person (10);
a reference parameter providing unit (60) for providing a reference parameter;
a correlation determining unit (30) for determining a degree of correlation between the first physiological parameter and the reference parameter;
a controller (40) for determining a control information based on the determined degree of correlation for controlling a light source unit (50),
wherein in a mode of operation of the system the control information is adapted to control the light source unit (50) by at least one of:
dimming the controllable light source unit and
changing the color of the light from the light source unit to warmer color tones having a lower color temperature when the degree of correlation increases.

Thereby, the person can increase his degree of relaxation based on his own physiological parameter(s) through the closed loop control formed by the elements of the system and based on an accurate control information through determination of the degree of correlation by the correlation determining unit. Thus, the modification of the degree of relaxation can be performed with increased accuracy using the determined degree of correlation.

Moreover, the light source unit can be comprised in the system or be external to the system. In the case that the light source unit is external to the system, the controller can then comprise recognition means for recognizing the light source unit, and thus allows the control information to be appropriately determined before being forwarded to the recognized light source unit. Furthermore, the light source unit is adapted to provide a positive feedback in response to the received control information and the system can be reversible for aiding a person who desires to relax or fall asleep to relax or fall asleep such that the degree of correlation tends to increase. In a further mode of operation the system can also be used for aiding a person who desires to wake up to wake up such that the degree of correlation tends to decrease.

The reference parameter providing unit may comprise a storing unit for storing a predetermined parameter as the reference parameter. Thereby, the degree of correlation can be determined even if a single physiological parameter of the person is determined.

The reference parameter providing unit may comprise a second physiological parameter determining unit for determining a second physiological parameter of the person as the reference parameter. Thereby, the degree of correlation can be determined between at least two physiological parameters of the person.

The first physiological parameter determining unit and the reference parameter providing unit may be integrated in an integrating unit, wherein the integrating unit determines the first physiological parameter and a second physiological parameter of the person as the reference parameter. Thereby, the first physiological parameter determination unit and the reference parameter providing unit can be combined together in an integrating circuit.

The integrating unit may comprise:
a sensor for generating a signal comprising contributions of the first physiological parameter and the second physiological parameter; and
an extracting unit for extracting from the signal of the sensor the first physiological parameter and the second physiological parameter. In this way, the first physiological parameter determining unit and the second physiological parameter determining unit can be implemented both as the sensor for measuring the signal and the extracting unit for extracting from the output of the sensor the first and second physiological parameters.

The sensor may comprise a piezoelectric foil being adapted to detect movements of the person caused by respiration and/or by heart movements of the person and to generate the signal based on the detected movements. By using a foil, the sensor can be easily integrated in the person's infrastructural environment while staying unobtrusive. Moreover, the sensor can be a piezoelectric transducer, i.e. a vibration sensor, adapted to detect any mechanical deformation like the chest motion, such that the measured signal can be the pulsing generated through the blood vessels, i.e. the heartbeats, as well as the body movement related to the respiration, i.e. the breathing or respiratory action.

The correlation determining unit may be adapted to determine a degree of coherence between the first physiological parameter and the reference parameter as the degree of correlation. Thereby, the degree of correlation can indicate the level of synchronization between the first physiological parameter and the reference parameter.

The degree of correlation may be determined through a comparison between the first physiological parameter and the reference parameter and a look-up table that stores a mapping function linking the comparison result to the degree of correlation.

The signal comprising contributions to the first physiological parameter and the reference parameter can be a non-periodic signal, and these parameters can be related to the skin temperature, the skin conductivity or galvanic skin response (GSR), or the physical activity of the person, i.e. if the person is moving a lot or is staying still.

The degree of correlation may be determined through a comparator that measures the phase shift between the first physiological parameter and the reference parameter and a look-up table that stores a mapping function linking the phase shift to the degree of correlation.

The signal comprising contributions to the first physiological parameter and the reference parameter can be a periodic signal, and these parameters can for example be vital parameters like the breathing or respiratory rate, the heart rate or the blood pressure.

The determination of the control information is further based on configurable settings stored in the controller. Thereby, the control information can be determined based on a combination between the determined degree of correlation and the configurable settings. The configurable settings can for example be related to preferences of the person in terms of light color, etc, as well as to the infrastructural environment of the person in which the system operates and also to physiological data of the person. Thus, the influence of infrastructural parameters, such as the wall colour or the presence of other light source devices not controlled by the controller through the control information can be taken into consideration for enhancing the positive biofeedback. The system may be further adopted to provide further control information for controlling further output units, such as e.g. speakers for providing audible feedback to the user. In such a system the influence of infrastructural parameters such as the room acoustics or the presence of other audio devices not controlled by the controller through the control information in the case that the output unit 50 is an acoustic unit, can be taken into consideration for enhancing the positive biofeedback. Both of the above modalities of feedback can be additionally based on appropriate physiological data of the person such as sleep quality, insomnia, etc, and the preferences of the person. Furthermore, the configurable settings can be determined using at least one sensing device, e.g. acoustical sensors like microphones or light sensors like photocells, being adapted to detect the infrastructural parameters related to the infrastructural environment of the person in which the system operates, such that the detection of the infrastructural parameters can be unobtrusively performed.

The system may further comprise the light source unit and more optionally one or more further output units adapted to be controllable by the control information for outputting the output signal for increasing the degree of relaxation of the person in one mode of operation.

The first physiological parameter and the reference parameter may be time-dependent and in this case, the correlation determining unit is adapted to determine a degree of correlation between the first physiological parameter and the reference parameter by following the steps of:

truncating the first physiological parameter and the reference parameter by capturing a plurality of samples of each of the first physiological parameter and the reference parameter over a same time window;

filtering each truncated parameter for removing the offset component;

normalizing each truncated and filtered parameter; and calculating the scalar product of the truncated, filtered and normalized first physiological parameter and the truncated, filtered and normalized reference parameter.

This allows determining the degree of correlation with a further approved accuracy.

In accordance with the present invention, there is also provided a method of controlling a light source unit for increasing a degree of relaxation of a person, the method comprising the steps of:

determining a first physiological parameter of the person;

providing a reference parameter;

determining a degree of correlation between the first physiological parameter and the reference parameter;

determining a control information based on the determined degree of correlation for controlling a light source unit (50), wherein the control information is adapted to control the light source unit (50) by at least one of:

dimming the light source unit and changing the color of the light from the light source unit to warmer color tones having a lower color temperature.

The present invention extends to a computer program for controlling a light source unit for increasing a degree of relaxation of a person, wherein the computer program comprises program code means for causing the aforementioned system to carry out the steps of the aforementioned method, when the computer program is run on a computer controlling the system.

It shall be understood that the aforementioned system, method and computer program have similar and/or identical preferred embodiments as defined in the dependent claims.

It shall be understood that a preferred embodiment of the invention can also be any combination of the dependent claims with the respective independent claim.

BRIEF DESCRIPTION OF THE DRAWINGS

These and other aspects of the invention will be apparent from and elucidated, by way of non-limitative examples, with reference to the embodiment(s) described hereinafter. In the following drawings:

FIG. 6 shows a schematic diagram illustrating the signal processing (truncation in FIG. 6A, filtering and normalization in FIG. 6B) for determining the degree of coherence between the different time-dependent physiological parameters HR, BR, the filtering comprising in particular removing the offset component (dashed line with an arrow);

DETAILED DESCRIPTION OF EMBODIMENTS

Figure 1:
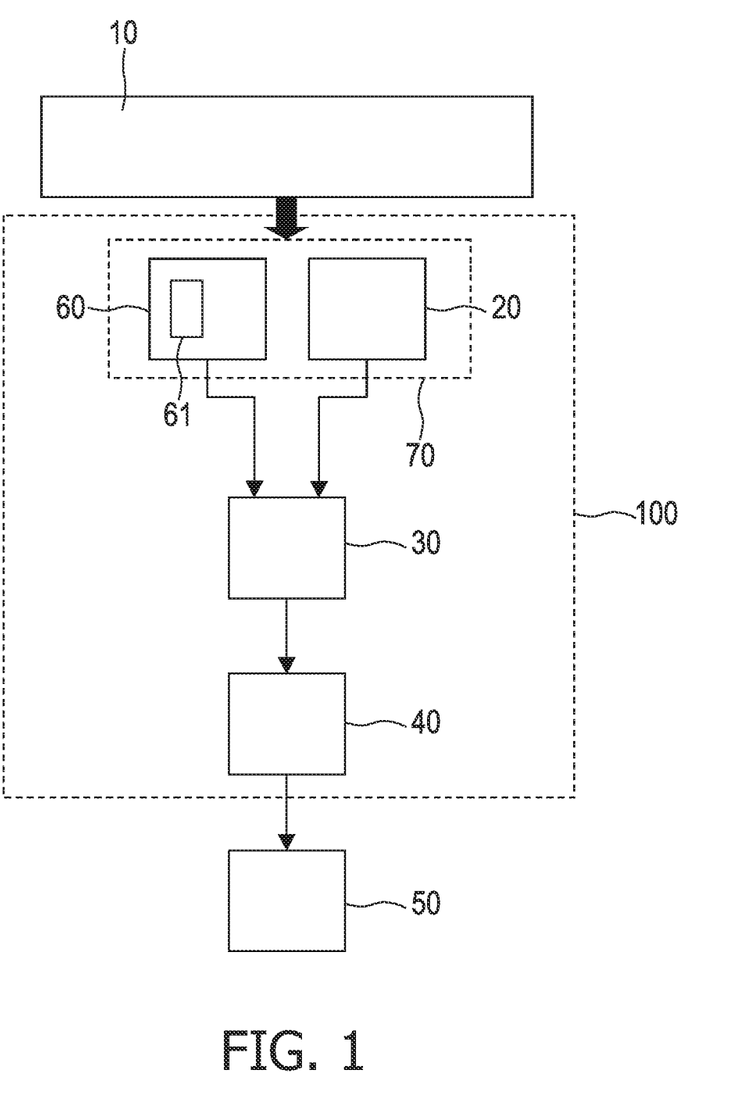
FIG. 1 shows a schematic diagram of a system (100) for modifying the degree of relaxation of a person (10) using biofeedback according to one embodiment of the present invention, wherein the first physiological parameter determining unit (20) and the reference parameter providing unit (60) are integrated in the integrating unit (70) (in dashed line)

FIG. 1 illustrates a schematic diagram of a system 100 according to one embodiment of the present invention for modifying the degree of relaxation of a person 10 using biofeedback, in order to aid him to relax or fall asleep if awaken, or wake up if fallen asleep. The system 100 comprises a first physiological parameter determining unit 20 for determining a first physiological parameter of the person 10, a reference parameter providing unit 60 for providing a reference parameter, a correlation determining unit 30 for determining a degree of correlation between the first physiological parameter and the reference parameter, and a controller 40 for determining a control information based on the determined degree of correlation, wherein the control information is adapted to control an output unit 50 for outputting an output signal for modifying the degree of relaxation of the person 10.

In the case that a single physiological parameter, i.e. the first physiological parameter, of the person 10 is determined, the reference parameter providing unit 60 can comprise a storing unit 61 for storing a predetermined parameter, e.g. temperature, galvanic skin response (GSR), heart rate (HR), breathing rate (BR) or an artificially generated parameter, as the reference parameter. Thereby, the determination of a degree of correlation between the first physiological parameter and the reference parameter can be made possible.

In the case that more than one physiological parameter, i.e. the second physiological parameter, of the person 10 is determined, the reference parameter providing unit 60 can comprise a second physiological parameter determining unit for determining a second physiological parameter of the person 10, e.g. temperature, galvanic skin response (GSR), heart rate (HR), breathing rate (BR), as the reference parameter. Thereby, the determination of a degree of correlation between the first physiological parameter and the second physiological parameter can be made possible.

In the case that more than one physiological parameter, i.e. the second physiological parameter, of the person 10 is determined, the first physiological parameter determining unit 20 and the reference parameter providing unit 60 can be combined together in order to be integrated in an integrating unit 70, which is then adapted to determine the first physiological parameter and the second physiological parameter as the reference parameter. Furthermore, such an integrating unit 70 can be regarded as a unit comprising a sensor 71 for generating a signal comprising contributions of the first physiological parameter and the second physiological parameter, and an extracting unit 72 for extracting from the output of the sensor (71) the first physiological parameter and the second physiological parameter. Thereby, the first physiological parameter determination unit 20 and the reference parameter providing unit 60 can be implemented as the sensor 71 and the extracting unit 72. This perspective on the integrating unit 70 is schematically and exemplarily shown in FIG. 2.

Figure 2:
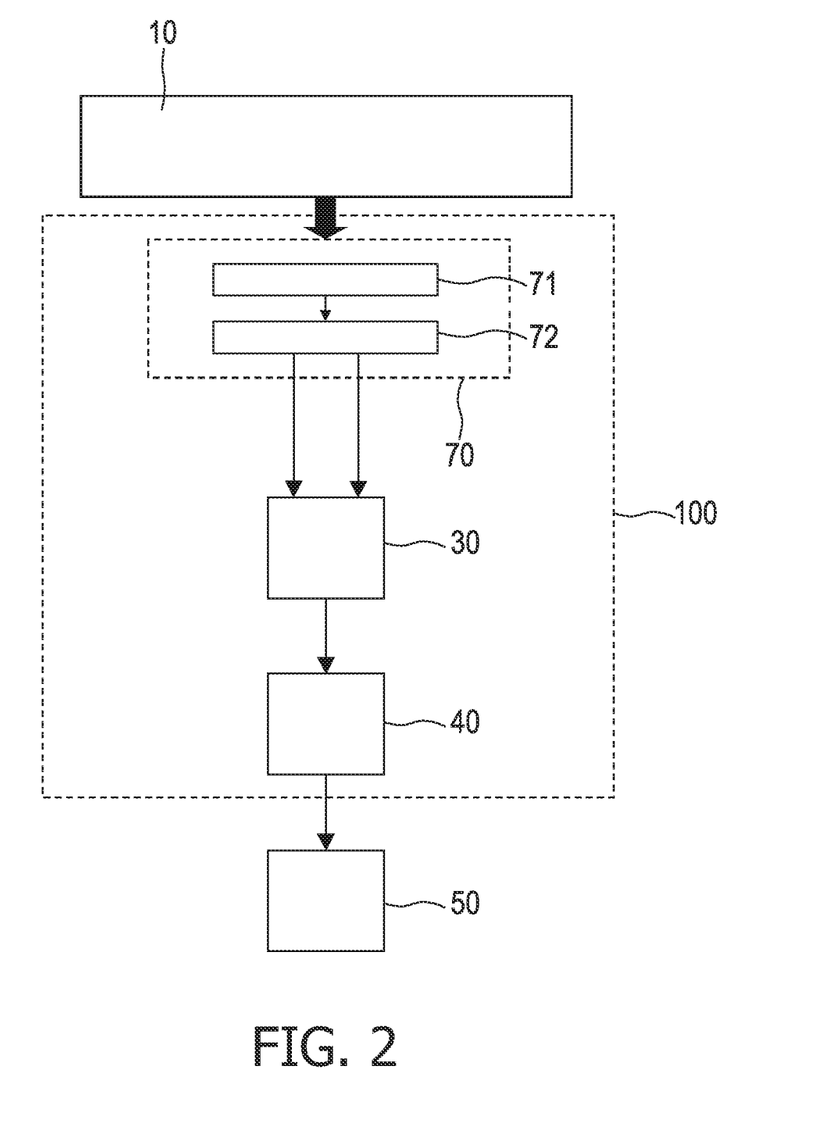
FIG. 2 shows a schematic diagram of the system (100) for modifying the degree of relaxation of a person (10) using biofeedback according to the embodiment of the present invention, wherein a sensor (71) and an extracting unit (72) are integrated in the integrating unit (70) (in dashed line)
Figure 3:
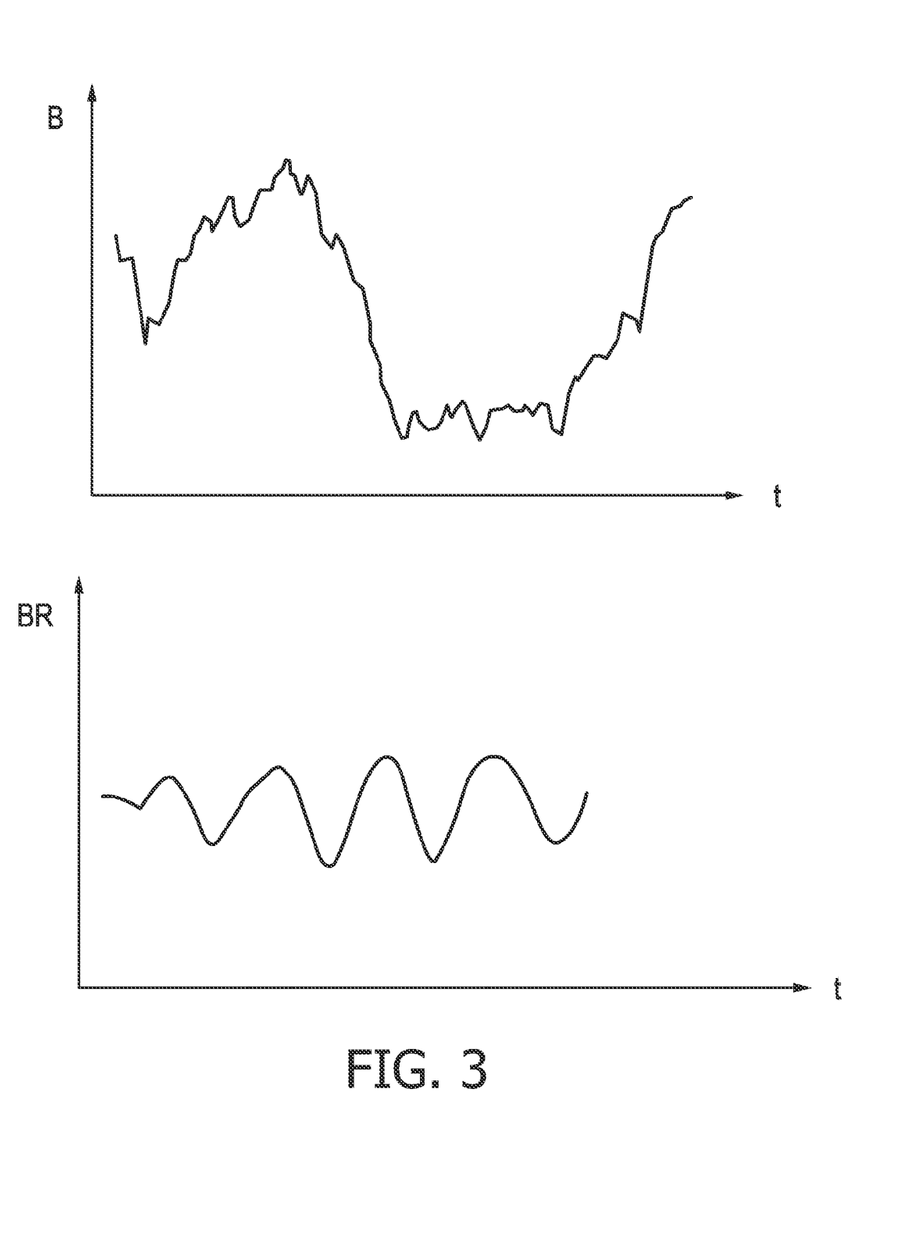
FIG. 3 shows a graph illustrating over time (t), the signal (B) provided by the first physiological parameter determining unit (20) of FIG. 1 in the upper trace, and in the lower trace, the signal component representing the breathing rate (BR) and extracted by low-pass filtering from the upper trace.
Figure 4:
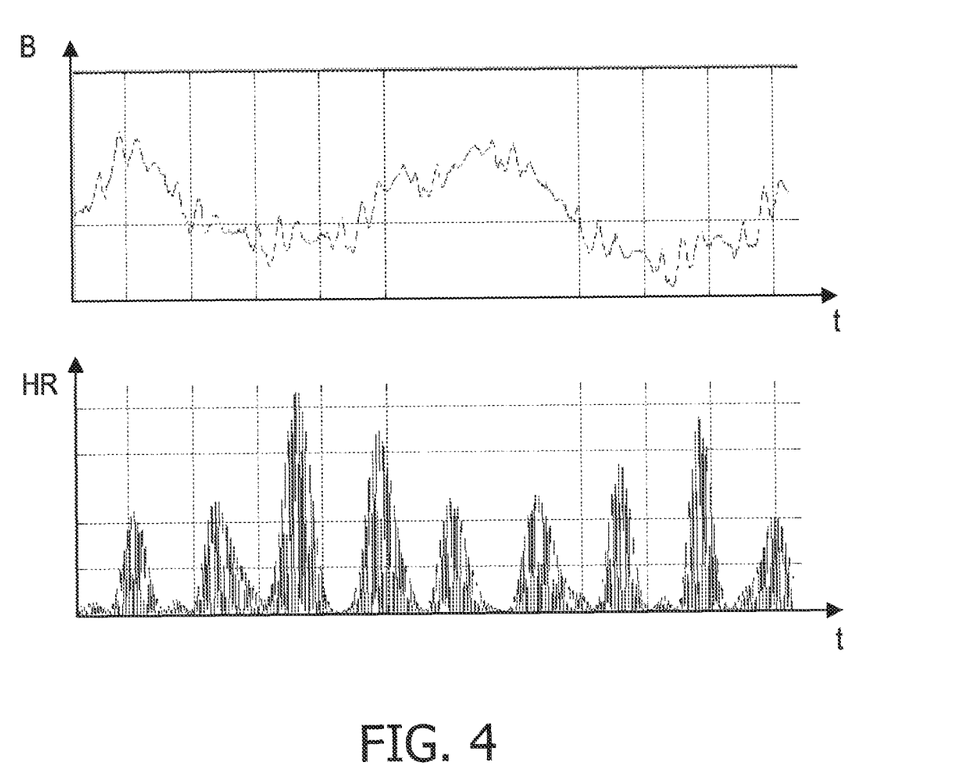
FIG. 4 shows a graph illustrating over time (t), the signal (B) provided by the first physiological parameter determining unit (20) of FIG. 1, and in the lower trace, the signal component representing the heart rate (HR) and extracted from the upper trace using an auto-correlation function.

In the illustrative case that the signal is the pulsing generated through the blood vessels, i.e. the heartbeat-induced impulses, as well as the body movement related to the respiration, i.e. the respiratory action, then the physiological parameters can respectively be the heart rate (HR) and the breathing rate (BR). In order to detect such mechanical deformation, the sensor 71 can be a vibration sensor like a piezoelectric transducer, e.g. a ferro-electret, which is a dielectric material exhibiting the property to detect a mechanical deformation and then to convert it into a voltage signal. The sensor 71 is preferably located under the chest of the person 10 for sensing the chest motion and has a sufficiently large area, preferably in a rectangular shape having a length and a width typically in a range from 300 mm to 600 mm, in order to properly detect and convert the signal. Moreover, the sensor 71 can also preferably be in an appropriate thin flat form, e.g. a foil or a polymer film, in order to be as unobtrusive as possible by being easily integrated in the person's infrastructural environment. In the particular case that the person 10 is in a bed, the sensor 71 can then be integrated in the bed sheet, the mattress or the bedstead. For example, the sensor 71 can be sewn into the bed sheet or slid into a textile pocket of the bed sheet for remaining hidden and well positioned under the chest, thereby enhancing a seamless integration into the bed environment. Thus, the technology fully integrates in the process of going to bed and falling asleep or being in bed and awaking. As illustrated in FIG. 3 wherein a ferro-electret foil has been positioned under the chest of the person 10 and underneath the bed sheet, the converted signal (upper trace) is a single voltage signal that is the superposition of a signal component, which corresponds to the respiratory action and represents the breathing rate BR (lower trace), and another signal component, which corresponds to the heartbeat-induced impulses and represents the heart rate HR. The splitting of the converted signal into the two separate signal components is carried out by the extracting unit 72. Thus, the signal component representing the breathing rate can be extracted from the converted signal by filtering, e.g. through a low-pass digital filter, and as illustrated in FIG. 4, the signal component representing the heart rate (lower trace) can be extracted from the converted signal (upper trace) using a correlation technique, e.g. by calculating an auto-correlation function of the converted signal in the time domain whose maxima indicate the instants when the heartbeats occurred.

The correlation determining unit 30 can then determine the degree of correlation between the different physiological parameters, i.e. the heart rate (HR) and the breathing rate (BR) in our illustrative case, represented by the separate signal components delivered by the integrating unit 70 through the extracting unit 72.

Figure 5:
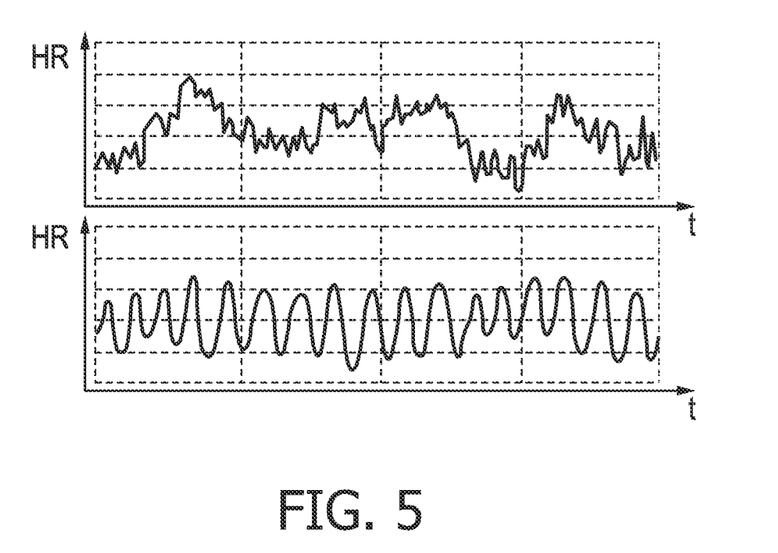
FIG. 5 shows a graph wherein the upper trace corresponding to a low degree of coherence depicts the variation of the heart rate (HR) of a stressed person over time (t), and the lower trace corresponding to a high degree of coherence depicts the variation of the heart rate (HR) of a relaxed person over time (t)

It is known in the art that the variation in time of the respiratory or breathing rate (BR) occurs in a sine wave manner. A high degree of coherence can be reached under certain resting conditions corresponding to a positive or relaxed mood of the person under consideration, namely when the heart rate variability (HRV), which refers to the beat-to-beat alterations in heart rate (HR), of healthy individuals also exhibits a periodic variation in a sine wave manner. This rhythmic phenomenon, known as respiratory sinus arrhythmia (RSA), fluctuates with the phase of respiration: cardio-acceleration during inspiration and cardio-deceleration during expiration. Thus, the heart rate (HR)

tends to synchronize with the person's breathing activity when the person—starting from an initial stressed or negative mood—gets into a relaxed or positive mood, thereby making possible to derive the respiratory rate (BR), i.e. the breathing frequency, from the sinusoidal variations of the heart rate (HR) since the respiration and heart rhythm patterns thereby become synchronous and operate at the same frequency. Conversely, the heart rate (HR) tends to de-synchronize with the person's breathing activity when the person—starting from an initial relaxed or positive mood—gets into a stressed or negative mood, thereby making impossible to derive the respiratory rate (BR), i.e. the breathing frequency, from the non-sinusoidal variations of the heart rate (HR). This is illustrated in FIG. 5, wherein the upper trace corresponding to a low degree of coherence depicts the variation of the heart rate (HR) of a stressed person over time, and the lower trace corresponding to a high degree of coherence depicts the variation of the heart rate (HR) of a relaxed person over time.

Furthermore, it is to be noted that the heart rate (HR) is also correlated with the person's mental and emotional states as it is illustrated in the paper of William A. Tiller, Rollin McCraty, and Mike Atkinson, entitled "Cardiac Coherence: A New Noninvasive Measure of Autonomic Nervous System Order", published in Alternative Therapies in Health and Medicine, 1996; 2(1): 52-65, wherein it can be seen that states of agitation, e.g. anger, anxiety or frustration, tend to cause disorder in the heart rate waveforms.

Thus, in our illustrative case, the correlation determining unit 30 can be adapted to determine the degree of coherence between the different time-dependent physiological parameters HR and BR representing the respective separate signal components.

Figure 6A:
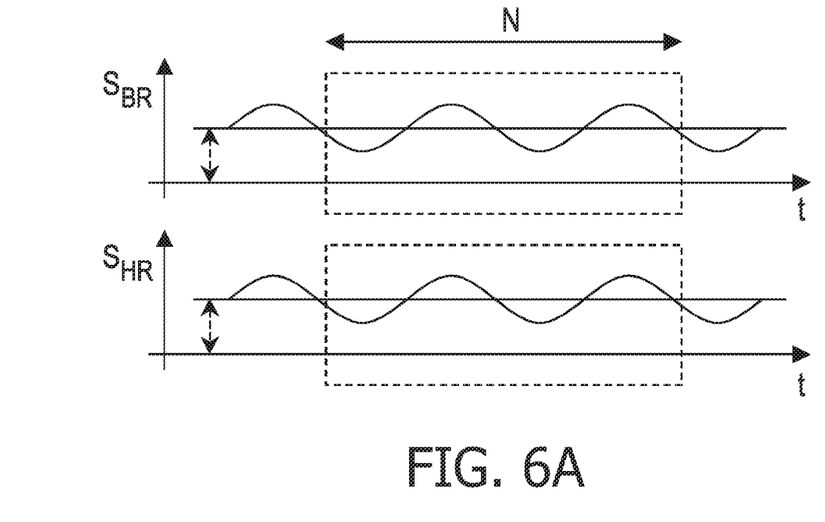
Figure 6B:
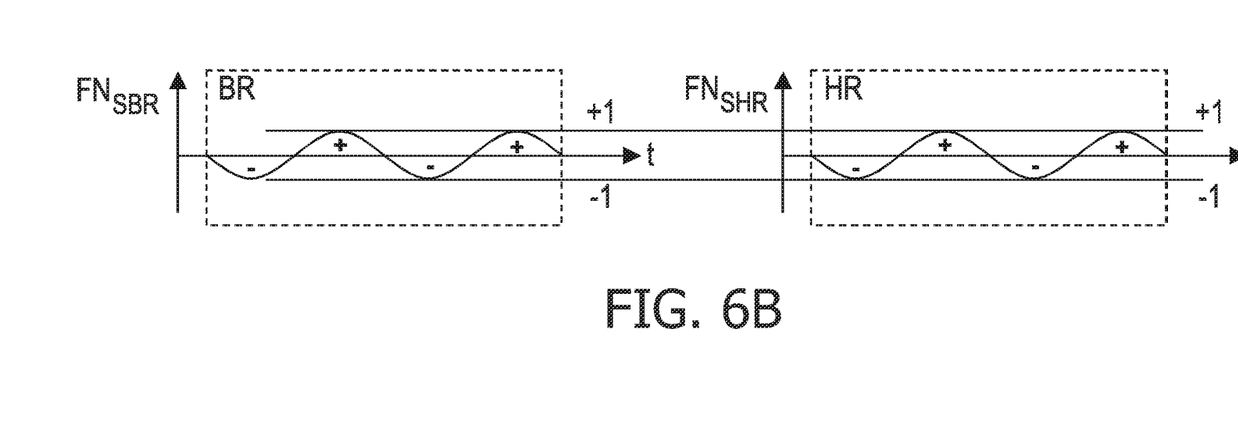

In an example, the degree of coherence can be determined by first capturing, over a same time window (dashed lines) as depicted in FIG. 6A, N samples of each separate signal component received from the integrating unit 70 through the extracting unit 72. Each truncated or portion of the separate signal components within the same time window is then filtered for removing its offset component (dashed line with an arrow), and in order to make a comparison between each of them, each portion of the filtered separate signal components $F_{SHR}$, $F_{SBR}$ is normalized, for example to unity, i.e. to |±1|, as depicted in FIG. 6B showing the graphs of the portions of the filtered and normalized separate signal components $FN_{SHR}$, $FN_{SBR}$ over time. Afterwards, the degree of coherence is calculated as the cross-correlation between these two portions of the filtered and normalized signal components $FN_{SHR}$, $FN_{SBR}$, following the scalar product of dimension N given by the relation (1):

$$\text{degree of coherence} = \sum_{i=0}^{N-1} FN_{SBR}(i) \cdot FN_{SHR}(i) \quad (1)$$

wherein N represents the number of samples of each separate signal component captured by the extracting unit 72 in the integrating unit 70 over the same time window.

As it can be observed in FIG. 6B, the degree of coherence will be the higher because the maxima in absolute value in the filtered and normalized signal component representing the breathing rate (BR) coincide with the maxima in absolute value in the filtered and normalized signal representing the heart rate (HR). From a mathematical standpoint, the relation (1) shows that the calculated degree of coherence will be high when the positive values of the portion of the filtered and normalized signal component representing the breathing rate (BR) are multiplied with the positive values of the portion of the filtered and normalized signal component representing the heart rate (HR), and the negative values of the portion of the filtered and normalized signal component representing the breathing rate (BR) are multiplied with the negative values of the portion of the filtered and normalized signal component representing the heart rate (HR). Thus, the maximum degree of coherence will be reached when all elements contributing to the sum calculation are positive, while the degree of coherence will decrease when maxima in one of both filtered and normalized signal components coincide with minima in the other filtered and normalized signal component, thereby giving a negative contribution to the sum calculation.

In another example, the degree of coherence can be determined by comparing the phase of these separate signal components using a comparator, which can measure the resulting phase shift, and by linking this resulting phase shift to a degree of coherence according to a mapping function stored in a look-up table.

It is to be noted that in a case other than the illustrative case wherein it cannot be possible to measure a phase shift and thereby a degree of coherence, the degree of correlation can be determined through a comparison between the different physiological parameters, i.e. the first physiological parameter and the reference parameter, and a look-up table that stores a mapping function linking the comparison result to the degree of correlation.

Based on the determined degree of correlation, the controller 40 can afterwards determine a control information, which is forwarded towards the output unit 50, e.g. a controllable light source unit, an acoustic unit, etc, that is adapted to modify the degree of relaxation of the person 10 in response to the received control information.

The control information can be adapted to control the output unit 50 in such a manner that, when the person 10 desires to relax, the degree of correlation tends to increase for thus enhancing the increase of the degree of relaxation of the person 10, and when the person 10 desires to wake up, the degree of correlation tends to decrease for thus enhancing the decrease of the degree of relaxation of the person 10. The output unit 50 can thereby provide a positive feedback to the person 10 and the system 100 can be made reversible for aiding a person to relax and/or fall asleep by giving feedback such that the degree of correlation tends to increase, or to wake up by giving feedback such that the degree of correlation tends to decrease.

The output unit 50 can comprise a plurality of separate controllable devices. Thus, the separate controllable devices can receive control information from the controller 40, which can be the same control information for each controllable device or which can be individual control information adapted for each controllable device, and be adapted to aid the person 10 either to fall asleep or wake up.

Figure 7:
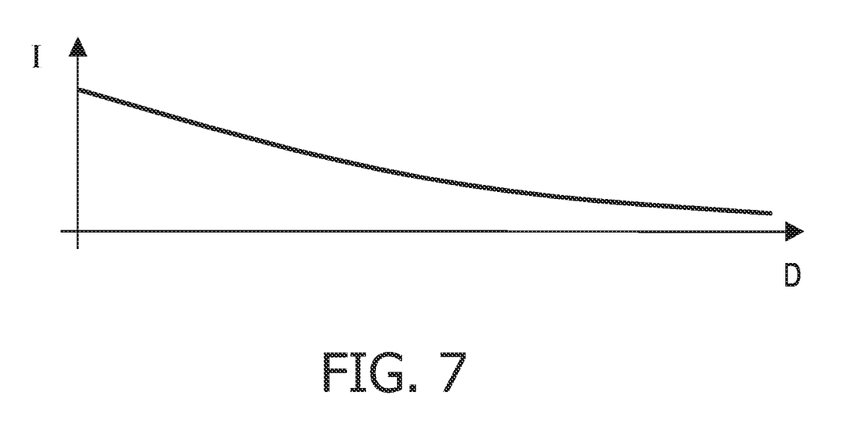
FIG. 7 shows a schematic diagram illustrating the control strategy of the controller (40) when controlling the brightness (I) of a controllable light source unit versus the degree of coherence (D)

In a first example, the control information can be provided to a controllable light source unit for controlling its light settings, e.g. color (C) and brightness/intensity (I), versus the degree of correlation according to a control strategy. Thus, in order to aid the person 10 to be further relaxed until falling asleep, FIG. 7 shows that, when the degree of coherence (D) between the different physiological parameters HR, BR tends to increase, namely when the relaxation state of the person 10 tends to increase, the controllable light source unit will be dimmed down according to, for example, a mathematical function for reducing the light brightness/ intensity (I) or maintaining the light brightness/intensity (I) at its dim level if the person 10 does not manage to relax. Conversely, in order to aid the person 10 to wake up, the controllable light source unit will be dimmed up when the degree of coherence (D) between the different physiological parameters HR, BR decreases, namely when the relaxation state of the person 10 decreases, according to, for example, a mathematical function for increasing the light brightness/intensity (I) or maintaining the light brightness/intensity (I) at its dim level if the person 10 does not manage to wake up. Independently or in a combined manner with the intensity dimming, the controllable light source unit can also modify its light color (C) towards warmer tones when the degree of coherence increases or colder tones when the degree of coherence decreases. Furthermore, in order to be as unobtrusive as possible, the controllable light source unit can be a light source already existing in the room, e.g. the lamp sitting on the bedside table if the person 10 is in his bedroom.

In a second example, the control information can be provided to an acoustic unit, e.g. a radio, a CD-player, a MP3-player or any other audio device, capable, if the person 10 desires to relax, of giving appropriate breathing instructions for enhancing relaxation or playing relaxing music so that the degree of correlation increases, namely so that the relaxation state of the person 10 increases, and conversely capable, if the person 10 desires to wake up, of giving appropriate breathing instructions for enhancing stress or playing non-relaxing music so that the degree of correlation decreases, namely so that the relaxation state of the person 10 decreases.

The output unit 50 can comprise a plurality of controllable devices, e.g. light source devices, acoustic devices, and any other device appropriate to modify the relaxation state of the person 10. If these controllable devices can be available in the infrastructural environment of the person 10, e.g. his bedroom, then the controller 40 can also be adapted to provide them separately or in a combined manner with the control information. The control information provided by the controller 40 can be the same control information for each controllable device or can be individual control information adapted for each controllable device.

The determination of the control information through the controller 40 can be based on a look-up table storing a mapping function linking the values of the degree of correlation to a level of intensity and/or of colour, such as the mathematical function of FIG. 7 for example. The determination can additionally be based on configurable settings stored in the controller 40, which can be related to the infrastructural environment of the person 10 in which the system 100 operates, physiological data of the person 10, and/or preferences of the person 10 in terms of music, light colour, etc. For example, the influence of infrastructural parameters, such as the wall colour or the presence of other light source devices not controlled by the controller 40 through the control information in the case that the output unit 50 is a controllable light source unit, or such as the room acoustics or the presence of other audio devices not controlled by the controller 40 through the control information in the case that the output unit 50 is an acoustic unit, can be taken into consideration for enhancing the positive biofeedback, as well as appropriate physiological data of the person 10 such as sleep quality, insomnia, etc, and the preferences of the person 10. Furthermore, the configurable settings can be determined using at least one sensing device, e.g. acoustical sensors like microphones or light sensors like photocells, being adapted to detect the infrastructural parameters related to the infrastructural environment of the person 10 in which the system 100 operates, such that the detection of the infrastructural parameters can be unobtrusively performed. Then, the control information can be determined based on a combination of the determined degree of correlation and the configurable settings.

It is to be noted that the output unit 50 can be comprised in the system 100 or alternatively external to the system 100. In the case that the output unit 50 is external to the system 100, the controller 40 can furthermore comprise recognition means for recognizing the output unit 50, and be so adapted to determine and forward appropriate control information towards the recognized output unit 50. For example, if the recognition means recognize a controllable light source unit and the person 10 desires to relax or fall asleep, the control information can be adapted for the controllable light source unit to dim down according to a mathematical function so that the degree of correlation between the different physiological parameters tends to increase, namely so that the relaxation state of the person 10 tends to increase.

It should be noted that, in the case that there are several persons 10 to be monitored in the same infrastructural environment, e.g. the bedroom, the system 100 allocated to each person 10 can be adapted to allow the communication between each controller 40. Thereby, the control information delivered by each controller 40 can be determined by further taking into account data, i.e. degree of correlation, configurable settings, etc, communicated by the other controllers 40. For example, the control information can then be determined based on an average value or a combined value between these respective communicated data.

Applications contemplated for such system 100 include any electronic aid for modifying the state of relaxation of a person 10 based on measurements of vital parameters and the degree of correlation between these parameters.

In summary, a system 100 for modifying a degree of relaxation of a person 10 using biofeedback has been described. The system 100 comprises a first physiological parameter determining unit 20 for determining a first physiological parameter of the person 10, a reference parameter providing unit 60 for providing a reference parameter, a correlation determining unit 30 for determining a degree of correlation between the first physiological parameter and the reference parameter, and a controller 40 for determining a control information based on the determined degree of correlation, wherein the control information is adapted to control an output unit 50 for outputting an output signal for modifying the degree of relaxation of the person 10.

Figure 8:
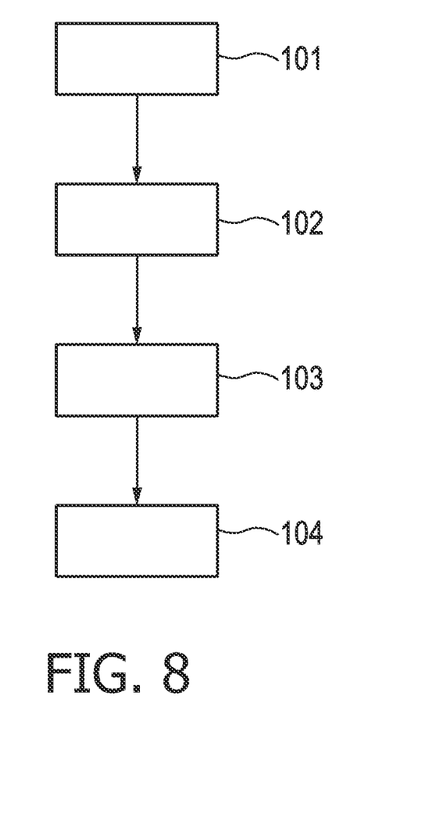
FIG. 8 shows a flow chart exemplarily illustrating a method for modifying a degree of relaxation of a person (10).

In the following a method for modifying a degree of relaxation of a person 10 will be described with reference to a flow chart shown in FIG. 8.

In step 101, a first physiological parameter of the person 10 is determined, and in step 102 a reference parameter is provided. In step 103, a degree of correlation between the first physiological parameter and the reference parameter is determined, and in step 104 a control information is determined based on the determined degree of correlation, wherein the control information is adapted to control an output unit for 50 outputting an output signal for modifying the degree of relaxation of the person 10.

While the invention has been illustrated and described in detail in the drawings and foregoing description, such illustration and description are to be considered illustrative or exemplary and not restrictive; the invention is not limited to the disclosed embodiments. For example, the present invention can generally be extended to any vital parameters exhibiting rhythmic patterns produced by different physiological oscillatory systems, e.g. not only the heart and respiratory rhythms but also the blood pressure oscillations, as well as the temperature, the Galvanic Skin Response (GSR), or the physical activity of the person, i.e. if the person is moving a lot or is staying still.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or devices may fulfill the functions of several items recited in the claims. The mere fact that certain measures are recited in mutually different dependent claims does not indicate that a combination of these measures cannot be used to advantage.

The calculations and determinations and/or the control of the system 100 in accordance with the above described method for modifying the degree of relaxation of a person can be implemented as program code means of a computer program and/or as dedicated hardware.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A light control system for increasing a degree of relaxation of a person, the system comprising:
   a first physiological parameter determining unit for determining a first physiological parameter of the person;
   a reference parameter providing unit for providing a reference parameter;
   a correlation determining unit for determining a degree of correlation between the first physiological parameter and the reference parameter;
   a controller for determining control information based on a combination of (i) the determined degree of correlation and (ii) configurable settings for controlling an output unit, wherein the output unit comprises a plurality of controllable devices selected from a light source unit, light source devices, acoustic devices and any other device appropriate to modify a relaxation state of the person, wherein the configurable settings are stored in the controller and relate to (a) an infrastructural environment of the person in which the system operates, (b) physiological data of the person, and (c) preferences of the person that include music and light color; and
   at least one sensing device adapted to detect infrastructural parameters of the infrastructural environment of the person in which the system operates, said infrastructural parameters including (a) a wall color, (b) a presence of at least one light source device not controlled by the controller through the control information, and (c) room acoustics or a presence of at least one audio device not controlled by the controller through the control information,
   wherein the controller is adapted to control the output unit based on the control information, and further wherein in a mode of operation of the system the controller is adapted to control the light source unit based on the control information by at least one of:
   dimming the light source unit, and
   changing a color of light of the light source unit to warmer color tones having a lower color temperature in response to an increase in the degree of correlation from a previously determined degree of correlation.

2. The system according to claim 1, wherein the reference parameter providing unit comprises a storing unit for storing a predetermined parameter as the reference parameter.

3. The system according to claim 1, wherein the reference parameter providing unit comprises a second physiological parameter determining unit for determining a second physiological parameter of the person as the reference parameter.

4. The system according to claim 3, wherein the first physiological parameter and the reference parameter are different physiological parameters and are chosen from heart rates and breathing rates, respectively.

5. The system according to claim 1, wherein the first physiological parameter determining unit and the reference parameter providing unit are integrated in an integrating unit, wherein the integrating unit determines the first physiological parameter and a second physiological parameter of the person as the reference parameter.

6. The system according to claim 5, wherein the integrating unit comprises:
   a sensor for generating a signal comprising contributions of the first physiological parameter and the second physiological parameter; and
   an extracting unit for extracting from the output of the sensor the first physiological parameter and the second physiological parameter.

7. The system according to claim 6, wherein the sensor comprises a piezoelectric foil being adapted to detect movements of the person caused by respiration and/or by heart movements of the person and to generate the signal based on the detected movements.

8. The system according to claim 1, wherein the correlation determining unit is adapted to determine a degree of coherence between the first physiological parameter and the reference parameter as the degree of correlation.

9. The system according to claim 1, wherein the degree of correlation is determined through a comparison between the first physiological parameter and the reference parameter and a look-up table that stores a mapping function linking the comparison result to the degree of correlation.

10. The system according to claim 1, wherein the degree of correlation is determined through a comparator that measures a phase shift between the first physiological parameter and the reference parameter and a look-up table that stores a mapping function linking the phase shift to the degree of correlation.

11. The system according to claim 1, further comprising the light source unit adapted to be controllable by the control information for outputting the output signal.

12. The system according to claim 1, wherein the first physiological parameter and the reference parameter are time-dependent and wherein the correlation determining unit is adapted to determine the degree of correlation between the first physiological parameter and the reference parameter by following the steps of:
   truncating the first physiological parameter and the reference parameter by capturing a plurality of samples of each of the first physiological parameter and the reference parameter over a same time window;
   filtering each truncated parameter for removing an offset component;
   normalizing each truncated and filtered parameter; and calculating a scalar product of the truncated, filtered and normalized first physiological parameter, and the truncated, filtered and normalized reference parameter.

13. A method of controlling a light source unit for increasing a degree of relaxation of a person, the method comprising the steps of:
determining a first physiological parameter of the person;
providing a reference parameter;
determining a degree of correlation between the first physiological parameter and the reference parameter;
determining, via a controller, control information based on a combination of (i) the determined degree of correlation and (ii) configurable settings for controlling an output unit, wherein the output unit comprises a plurality of controllable devices selected from a light source unit, light source devices, acoustic devices and any other device appropriate to modify a relaxation state of the person, wherein the configurable settings are stored in the controller and relate to (a) an infrastructural environment of the person in which the method operates, (b) physiological data of the person, and (c) preferences of the person that include music and light color;
detecting infrastructural parameters, via at least one sensing device, of the infrastructural environment of the person in which the method operates, said infrastructural parameters including (a) a wall color, (b) a presence of at least one light source device not controlled by the controller through the control information, and (c) room acoustics or a presence of at least one audio device not controlled by the controller through the control information; and
controlling, via the controller, the output unit based on the control information, wherein controlling further includes controlling the light source unit based on the control information by at least one of:
dimming the light source unit, and
changing a color of light from the light source unit to warmer color tones having a lower color temperature in response to an increase in the degree of correlation from a previously determined degree of correlation.

14. The method according to claim 13, further comprising determining a second physiological parameter of the person as the reference parameter.

15. The method according to claim 13, wherein the first physiological parameter and the reference parameter are different physiological parameters and are chosen from heart rates and breathing rates, respectively.

16. The method according to claim 13, further comprising determining a degree of coherence between the first physiological parameter and the reference parameter as the degree of correlation.

17. The method according to claim 13, wherein the step of determining a degree of correlation comprises the steps of comparing the first physiological parameter and the reference parameter, and using a look-up table that stores a mapping function to link the comparison result to the degree of correlation.

18. The method according to claim 13, wherein determining the degree of correlation comprises measuring, via a comparator, a phase shift between the first physiological parameter and the reference parameter, and linking, via a look-up table that stores a mapping function, the phase shift to the degree of correlation.

19. The method according to claim 13, wherein the first physiological parameter and the reference parameter are time-dependent and wherein determining the degree of correlation between the first physiological parameter and the reference parameter comprises the steps of:
truncating the first physiological parameter and the reference parameter by capturing a plurality of samples of each of the first physiological parameter and the reference parameter over a same time window;
filtering each truncated parameter for removing an offset component;
normalizing each truncated and filtered parameter; and
calculating a scalar product of the truncated, filtered and normalized first physiological parameter, and the truncated, filtered and normalized reference parameter, wherein the degree of correlation comprises the scalar product.

20. A computer program stored on a non-transitory computer readable medium and executable via a controller for controlling a light source for increasing a degree of relaxation of a person, the computer program comprising the steps of:
determining a first physiological parameter of the person;
providing a reference parameter;
determining a degree of correlation between the first physiological parameter and the reference parameter;
determining control information based on a combination of (i) the determined degree of correlation and (ii) configurable settings for controlling an output unit, wherein the output unit comprises a plurality of controllable devices selected from a light source unit, light source devices, acoustic devices and any other device appropriate to modify a relaxation state of the person, wherein the configurable settings are stored in the controller and relate to (a) an infrastructural environment of the person in which the method operates, (b) physiological data of the person, and (c) preferences of the person that include music and light color;
detecting infrastructural parameters, via at least one sensing device, of the infrastructural environment of the person, said infrastructural parameters including (a) a wall color, (b) a presence of at least one light source device not controlled by the controller through the control information, and (c) room acoustics or a presence of at least one audio device not controlled by the controller through the control information; and
controlling the output unit based on the control information, wherein controlling further includes controlling the light source unit based on the control information by at least one of:
dimming the light source unit, and
changing a color of light from the light source unit to warmer color tones having a lower color temperature in response to an increase in the degree of correlation from a previously determined degree of correlation.

* * * * *